United States Patent [19]

Brown et al.

[11] E Patent Number: Re. 33,164

[45] Reissued Date of Patent: Feb. 13, 1990

[54] INFLUENZA VACCINE PRODUCTION IN LIQUID CELL CULTURE

[75] Inventors: Karen K. Brown, Kansas City, Mo.; Richard C. Stewart, Merriam, Kans.

[73] Assignee: Mobay Corporation, Pittsburgh, Pa.

[21] Appl. No.: 15,827

[22] Filed: Feb. 18, 1987

Related U.S. Patent Documents

Reissue of:

[64] Patent No.: 5,005,139
Issued: Feb. 19, 1985
Appl. No.: 428,495
Filed: Sep. 29, 1982

U.S. Applications:

[63] Continuation-in-part of Ser. No. 39,236, May 15, 1979, abandoned.

[51] Int. Cl.[4] ..... A61K 39/12; C12N 7/00; C12N 7/02; C12N 7/04

[52] U.S. Cl. ..... 424/89; 435/235; 435/236; 435/237; 435/238; 435/239

[58] Field of Search ..... 424/89; 435/235–239

[56] References Cited

U.S. PATENT DOCUMENTS

| | | | |
|---|---|---|---|
| 3,060,094 | 10/1962 | Dutcher et al. | 435/235 |
| 3,616,203 | 10/1971 | Brown | 435/235 |
| 3,655,871 | 4/1972 | Werner | 435/235 |
| 3,933,585 | 1/1976 | McAleer et al. | 435/235 |
| 3,959,074 | 5/1976 | Miller et al. | 435/235 |
| 3,965,258 | 6/1976 | McAleer et al. | 435/235 |
| 4,070,453 | 1/1978 | Bordt et al. | 435/235 |
| 4,080,258 | 3/1978 | McAleer et al. | 435/235 |
| 4,205,131 | 5/1980 | Almeida | 435/235 |

OTHER PUBLICATIONS

Klenk et al., Virology 68, 426–439 (1975).
Lazarowitz et al., (I), Virology, 68, 440–454 (1975).
Lazarowitz et al., II, Virology 52, 199–212 (1973).
Effect of Trypsin on Reproduction of Type 4 Parainfluenza Virus in Vero Cell Cultures Under Fluid Overlay—Morimoto et al.-pp. 1–11, Japan. J. Med. Sci. Biol., 23, 1970.
Effect of Trypsin on Viral Susceptibility of Vero Cell Cultures-Cercopithecus Kidney Line-Itoh et al.-pp. 227–235, 1970, Japan J. Med. Sci. Biol., 23, 1970.
Genetic Recombination for Antigenic Markers of Antigenically Different Strains of Influenza B Virus-Tobita et al.—pp. 347–352, Journal of Virology-Feb. 1974.
The Use of a Continuous Cell Line for the Isolation of Influenza Viruses-Davies et al.-pp. 991–993, Bulletin of the World Health Organization 56(6) (1978).
Identification of the Defective Genes in Three Mutant Groups of Influenza Virus-Ritchey et al.-pp. 1196–1204, Journal of Virology, 21(3) (1977).
Activation of Influenza A Viruses by Trypsin Treatment-Klenk et al., pp. 426–430-Virology 68, (1975).

*Primary Examiner*—Christine M. Nucker
*Attorney, Agent, or Firm*—Joseph C. Gil; Lyndanne M. Whalen

[57] ABSTRACT

Infectivity and replication of influenza viruses in successive numbers of cells of the same liquid cell culture is assured by including a protein hydrolyzing enzyme in the culture during virus incubation. Technique overcomes "one-step growth cycle" of virus and allows commercial influenza vaccine production from liquid cell cultures instead of from more costly embryonated chicken eggs. Resulting vaccine is thus substantially free of egg proteins.

34 Claims, 1 Drawing Sheet

FIG. 1 MIAMI ($A_2$)
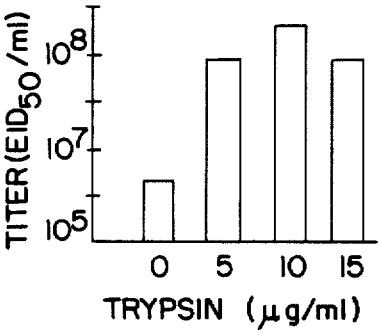
FIG. 2 PENN. ($A_1$)
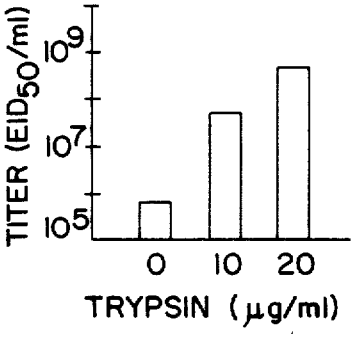
FIG. 3 B/HONG KONG
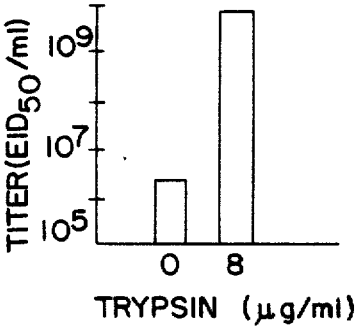
FIG. 4 A/TEXAS
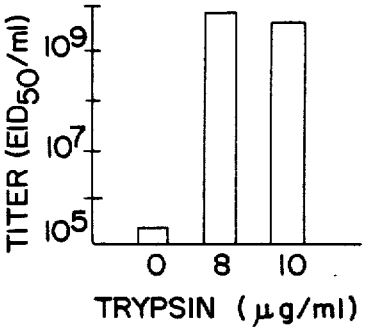
FIG. 5 A/USSR
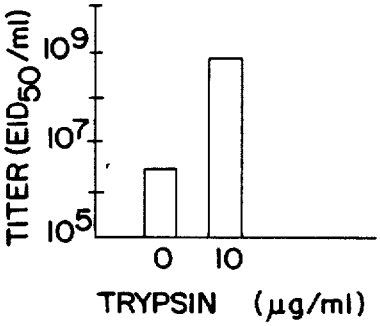

INFLUENZA VACCINE PRODUCTION IN LIQUID CELL CULTURE

Matter enclosed in heavy brackets [ ] appears in the original patent but forms no part of this reissue specification; matter printed in italics indicates the additions made by reissue.

This application is a continuation-in-part application of Ser. No. 039,236, filed May 15, 1979, abandoned.

BACKGROUND OF THE INVENTION

1. Field

This disclosure is concerned generally with a novel influenza virus propagation medium and specifically with the use of that medium for influenza vaccine production.

2. Prior Art

Influenza vaccines have been in use since the early 1940's for human vaccination and since the late 1960's for equine vaccination. All influenza vaccines presently used are made by growing the vaccine virus strains in embryonated chicken eggs. The resulting virus strains are then used for making live virus vaccines or further processed to make killed virus vaccines.

It is generally known by virologists that influenza viruses grow to a very limited degree in cell cultures. The growth is referred to as a "one-step growth cycle"; that is, only the originally infected cells replicate viruses. This phenomenon is described, for example, by Davis et al., MICROBIOLOGY, Harper and Row Publishers, Chapter 44, pp. 1138–39 (1968). Since the viruses of the originally infected cells are unable to infect successive numbers of cells in the same cell culture, the resulting yields are far too low to be useful in the preparation of virus vaccines. Thus, liquid cell cultures have not been used for commercial production of influenza virus vaccines.

Embryonated chicken eggs are used to produce viruses with titers sufficiently high enough to be useful in the preparation of vaccines. Unfortunately, chick embryo-grown viruses usually require concentration, and, in the case of human vaccines, also require some form of purification to reduce toxic reactions due to the undesirable egg proteins. The use of the eggs for vaccine production is time consuming, labor intensive, requires relatively high material costs, and the yield from one egg is commonly only enough to produce vaccine for about one to 1.5 doses. Thus, the manufacture of millions of doses requires innoculating and harvesting millions of embryonated eggs.

Recently, it has been noted that a wide variety of influenza A viruses comprising human, equine, porcine, and avian strains, grew productively in an established line of canine kidney cells under an overlay medium containing trypsin and formed well-defined plaques regardless of their prior passage history. See the article by K. Tobita et al., "Plaque Assay and Primary Isolation of Influenza A Viruses in an Established Line of Canine Kidney Cells (MDCK) in the present of Trypsin", Med. Microbiol. Immunol. 162, 9–14 (1975). See also the article by Hans-Dieter Klenk et al., "Activation of Influenza A Viruses by Trypsin Treatment", Virology 68, 426–439 (1975). It should be noted that in the above reports the effects of trypsin on influenza virus propagation were observed in semi-solid cultures in plaque formation assays and isolation techniques, neither of which are concerned with liquid cell cultures or the large scale or commercial propagation of influenza viruses for vaccine production. The term liquid cell culture used herein describes the in vitro growth of cells and propagation of virus in a chemically defined liquid medium.

Quite surprisingly, we have now found that proteolytic enzymes can also be used in liquid cell cultures to facilitate infection of successive numbers of cells in the same cell culture. By thus overcoming the limitations of the "one-step growth cycle" of past liquid cell culture techniques, it is possible to achieve an influenza virus yield which is in the range of about 1,000 to 10,000 fold greater than non-protease treated cultures. This makes feasible the use of liquid cell culturing techniques for the commercial production of influenza vaccines, thereby avoiding the disadvantages associated with using embryonated chicken eggs. Details of our culturing medium, virus propagation techniques, and vaccine production and use methods are disclosed herein.

SUMMARY OF THE INVENTION

Our influenza virus propagation medium comprises a cell culture capable of being infected with an influenza virus, an influenza virus, and a protein-hydrolyzing enzyme, the amount of enzyme being sufficient to overcome the one-step growth cycle of the virus. Our virus propagation technique comprises the steps of inoculating or infecting a liquid influenza virus cell culture with the influenza viruses, incubating the inoculate in the presence of a protein-hydrolyzing enzyme under conditions sufficient to assure maximum virus growth (or maximum cytopathic effect) and harvesting the virus. Infection of the cells with the virus may occur before or after cell monolayer formation or, alternatively, by simply infecting a liquid suspension of the cells. Our vaccine production method includes the subsequent step of killing the harvested virus or attenuating by further cell culture passage for vaccine use. Especially preferred embodiments involve the use of the protease trypsin in conjunction with a dog kidney cell line to propagate any of several types of influenza viruses.

BRIEF DESCRIPTION OF THE FIGURES

FIGS. 1–5 are bar graphs illustrating the increases in titer achieved when the indicated virus strains were incubated in a liquid cell culture in the presence of various amounts of a typical protease, trypsin. Results are reported as geometric mean titers.

SPECIFIC EMBODIMENTS

The influenza virus and vaccine production techniques of this disclosure contemplate the use of influenza vaccine viruses. As used herein, the term influenza virus includes any viruses capable of causing a febrile diease state in animals (including man) marked by respiratory symptoms, inflamation of mucous membranes and often systemic involvement. The medium and methods of this disclosure are especially useful in the production of a variety of influenza viruses, including human, equine, porcine, and avian strains. Examples of the production of typical Type A and B Influenza viruses are described below.

The vaccine preparations contemplates by this disclosure include any preparation of killed, living attenuated, or living fully virulent influenza viruses that can be administered to produce or artificially increase immunity to any influenza disease. In preferred embodiments, the vaccine comprises an aqueous suspension of the virus particles in ready to use form.

The cell cultures contemplated as being useful in carrying out the principles of this disclosure include any animal cell line or cell strain capable of being infected by, and which allows the replication of, one or more given influenza virus strains. Although a number of such cells are known and thought to be useful for the techniques disclosed herein, we have had especially good results with an established cell line known as the Cutter Laboratories Dog Kidney (CLDK) cell line. The CLDK cell line has been approved by the U.S. Department of Agriculture for use in producing veterinary vaccines and is similar to the madin Darby Dog Kidney Cell Line (ATCC No. CCL 34) and to the dog kidney cell line described in U.S. Pat. No. 3,616,203 to A. Brown. A brief history and description of the specific master cell stock used for the cell line of the Examples follows although it should be understood that the techniques disclosed herein are thought to be useful with any influenza virus susceptible cell culture.

CUTTER LABORATORIES DOG KIDNEY (CLDK) CELL LINE HISTORY

The parent line of CLDK was initiated and established at Cutter Laboratories, Inc., Berkeley, Calif. from the kidney of an apparently normal beagle dog obtained from the University of California at Davis. The line was maintained on 0.5% lactalbumin hydrolysate and 0.2% yeast extract in Earle's balanced salt solution plus 5% calf, lamb, or horse serum and antibiotics, cultivated by the methods of J. S. Younger (Proc. of Exp. Biol., and Med., v 85 202).

A frozen ampoule of the 142nd passage of this cell line was subsequently planted in a 75 $cm^2$ (250 ml) falcon flask, in tissue culture medium consisting of Earle's balanced salt solution Minimum Essential Medium (MEM) and 10% fetal bovine serum. The cells were subcultured in the same manner and medium to prepare the frozen Master cell stock at passage 148.

An ampoule of the Master cell stock was thawed, planted, and serially subcultured 20 times to obtain bottle cultures of the 168th passage. These cells were then frozen.

DESCRIPTION OF MASTER CELL STOCK (MSC)

Number of Serial Subcultures from Tissue of Origin: 148

Freeze Medium: Minimum essential medium (Eagle) in Earle's BSS with reduced bicarbonate (1.65 gm/L) 80%; fetal bovine serum 10%; dimethyl sulfoxide 10%.

Viability: Approximately 75% (dye exclusion).

Culture Medium: Minimum essential medium (Eagle) in Earle's BSS with reduced bicarbonate (1.65 gm/L) 90%; fetal bovine serum 2–10%; antibiotic penicillin and streptomycin 100 U. or $\gamma$/ml.

Growth Characteristics of Thawed Cells: An inoculum of $3\times10^6$ viable cells/ml cultured in the above culture medium at 37° C. in a closed system, multiplies approximately 6–8 fold in 5 days.

Morphology: Epithelial-like.

Karyology: Chromosome Frequency Distribution 100 Cells: 2N=72.

| Cells | 1 | 1 | 2 | 4 | 6 | 9 | 69 | 5 | 3 |
|---|---|---|---|---|---|---|---|---|---|

-continued

| Chromosomes | 60 | 65 | 68 | 69 | 70 | 71 | 72 | 73 | 74 |
|---|---|---|---|---|---|---|---|---|---|

No marker chromosomes.

Sterility Tests: Free of Mycoplasma, bacteria and fungi.

Species: Confirmed as canine by immunofluorescence test.

Virus Susceptibility: Susceptible to influenza viruses, rabies virus, infectious bovine rhinotrachetis, infectious canine hepatitis, canine distemper virus, and possibly other viruses.

The protein hydrolyzing enzymes (proteolytic enzyme or protease) contemplated as being useful for purposes of this disclosure include well known proteases such as trypsin, chymotrypsin, pepsin, pancreatin, papain, pronase, carboxypeptidase, and the like, with trypsin being an especially preferred enzyme. The exact mechanism(s) by which a protease such as trypsin enhances the influenza virus infectivity is not fully known. One possible mechanism has been suggested in the above cited article by Klenk et al.

As described below, the amount of active protease required to enhance successive infectivity should be at least enough to overcome the limitations of the one-step growth cycle but, in the case of confluent monolayer cultures, not so much as to cause a sloughing of confluent cells from the surfaces of the tissue cultivation vessel (i.e. the inner surface of a roller bottle). In the case of the specific enzyme used in the examples below, we prefer that the amount of the enzyme be in the range of about 4 to 25 micrograms per ml ($\mu$g/ml) of liquid tissue culture medium, preferably about 10 $\mu$g/ml.

VIRUS PROPAGATION METHODS

The influenza virus propagation method of this disclosure comprises the three general steps of infecting a portion of the cells of a liquid cell culture with the influenza virus, incubating the cells in the presence of a proteolytic enzyme under conditions sufficient to assure maximum cytopathic (CP) effect, and harvesting the viruses from the culture. Vaccine preparation comprises the subsequent step of modifying the harvested virus by known techniques to result in a live virulent, attenuated, or killed (inactive) vaccine preparation. The vaccine may be available in dry form, to be mixed with a diluent, or in liquid, ready to use form. Suitable adjuvants may be included, as described below, to enhance immunogenicity.

The protease may be added to an aqueous suspension cell culture or before or after formation of a confluent monolayer culture. Examples of some of the various propagation methods are described below.

METHOD A-Infection of Pre-formed Monolayers

1. Cells are grown to confluency in culture containers such as roller bottles, Povitsky flasks, or Roux bottles utilizing cell culture growth media known to the art.

2. Prior to infection, the growth medium is removed from the cell monolayers.

3. The influenza virus working seed is diluted in growth medium containing additional vitamins, nonessential amino acids, L-glutamine, dextrose, and antibiotics with the pH adjusted to 6.6–6.8.

4. A quantity of the diluent containing virus is added to the cell monolayer in quantities ranging from 10% to 100% of the final harvest volume.

5. The infected monolayers are incubated at 34°-37° C. for 1 to 72 hours.

6. Protease, alone or in combination with the virus propagation media, is added at a concentration which will stimulate multiple cycle growth without producing cell slough. For trypsin, this optimum concentration is between about 8 and 15 μg/ml.

7. The virus growth containers are once again incubated at 34°-37° C. until maximum cytopathic effects are observed. At this point the virus fluids are harvested.

8. Harvest involves shaking the containers vigorously to remove cells and transferring fluids and cells to a sterile container for further processing.

METHOD B-Infection of Liquid Cell Suspension Prior to Monolayer Formation

1. Cells are removed from growth containers using conventional procedures.

2. Cells are concentrated by centrifugation, then resuspended in a quantity of fresh growth medium containing additional vitamins, non-essential amino acids, L-glutamine, dextrose, and antibiotics.

3. Influenza virus is then added to this concentrated cell suspension.

4. The cell virus suspension is incubated (25° C.-37° C.) in a sterile, closed container (such as a screwcap Ehrlenmeyer flask) while being mixed on a magnetic type stirrer or rotary shaker for 10 minutes to 4 hours.

5. Aliquots of the cell virus suspension are placed into growth containers (roller bottles, Roux bottles, Povitsky flasks) with the full volume of media containing ingredients indicated in B-2 plus 5% fetal calf serum.

6. Growth containers are incubated at 34°-37° C. until confluent monolayers are formed (approximately 2-4 days).

7. After monolayers have formed, protease is added at a concentration which will stimulate multiple cycle growth without producing cell slough. For trypsin, this optimum concentration is between 10 and 25 μg/ml.

8. Growth containers are incubated at 34°-37° C. until maximum cytopathic effects are observed. Virus is then harvested.

9. Harvest involves shaking containers vigorously to remove cells and transferring cells and fluids to a sterile container for further processing.

METHOD C-Infection of Liquid Suspension Culture

1. Cells adapted to suspension culture are grown to an optimum count in growth medium in suspension growth containers.

2. Cells are centrifuged and resuspended in a quantity of fresh medium containing additional vitamins, non-essential amino acids, L-glutamine, dextrose, and antibiotics.

3. Influenza virus is then added and the culture is incubated at 34°-37° C. for 10 minutes to several hours.

4. Fetal calf serum may be added and the culture suspension is further incubated at 34°-37° C. for 1 to 72 hours.

5. Protease is added at a concentration which will allow multiple cycle growth without producing a detrimental effect on the cells. For trypsin, the optimum concentration is between 4 and 25 μg/ml.

6. Incubation at 34°-37° C. is continued until maximum cytopathic effects are observed at which time fluids are harvested.

7. Harvest involves transfer of fluids to a sterile container for further processing.

Specific examples of the use of our techniques and media for the propagation of selected strains of influenza viruses follow. Unless otherwise indicated, we used conventional tissue culturing techniques known to the art. Since, both the cell and medium preparation techniques are well known, they are not described here in detail.

EXAMPLE 1

The A2 Equine Influenza Virus, designated Miami strain, was originally isolated from a horse at the University of Miami. This virus was obtained from the University of Pennsylvania Medical School where six passages were made in chick embryo. The seventh passage was made at and obtained from Lederle Laboratories. The strain underwent further chick embryo passage and was used at passages 11-16.

The present preferred method of tissue culture propagation of the A2 strain involves infection of a young, confluent monolayer of CLDK cells. Cells are planted in roller bottles, using Hank's Minimum Essential Medium (MEMH) containing the following ingredients:

Fetal Bovine Serum, 5-10%
Non-Essential Amino Acids, 10 ml/l (Gibco)
L-Glutamine, 10 ml/l (Gibco)
Neomycin Sulfate, 30,000 mcg/l
Polymyxin B, 30,000 units/l
Mycostatin, 25,000 units/l The cells are usually confluent with 72 hours at which time the medium is poured off and the cells are infected. The inoculating medium contains A2 virus diluted to an Egg Infective $Dose_{50}$ ($EID_{50}$) titer of approximately $10^{3.0}$/ml in MEMH supplemented with the following ingredients:

50% Dextrose, 2.6 ml/l
MEM Vitamins, 30 ml/l (Gibco)
Non-Essential Amino Acids, 10 ml/l (Gibco)
L-Glutamine, 10 ml/l (Gibco)
Neomycin Sulfate, 30,000 mcg./l
Polymyxin B, 30,000 units/l
Mycostatin, 25,000 units/l Inoculating medium equivalent to 14% of the final volume is added to each roller bottle and the containers are incubated at 34°-35° C. for 72 hours. At this time, the remaining medium (86%) containing 12 μg/ml of sterile trypsin (Sigma, 1:250) solution (0.1 g/100 ml), is added to each roller bottle. Containers are again incubated at 34°-35° C. until maximum cytopathic effect is observed (48-72hours) at which time the fluids are harvested. Harvest involves vigorously shaking each roller bottle to remove any attached cells and transferring cells and virus fluids to a sterile batching container for further processing.

Harvest $EID_{50}$ titers of A2 Influenza Virus grown using this technique are shown in Table 1. Also, see FIG. 1. A comparison is made with A2 virus grown by the same method but without adding trypsin.

TABLE 1

$EID_{50}$ OF MIAMI STRAIN EQUINE INFLUENZA VIRUS GROWN IN CLDK CELLS WITH AND WITHOUT TRYPSIN

| Amt. Trypsin (μg/ml) | Titer ($EID_{50}$/ml) Input | Harvest | Fold Increase With Trypsin |
|---|---|---|---|
| None | $10^{2.6}$ | $10^{6.2}$ | — |
| None | $10^{3.2}$ | $10^{6.2}$ | — |
| 5 | $10^{2.9}$ | $10^{8.3}$ | 126 |
| 5 | $10^{2.9}$ | $10^{8.1}$ | 79 |
| 5 | $10^{2.6}$ | $>10^{9.2}$ | >1.000 |

TABLE 1-continued

| EID$_{50}$ OF MIAMI STRAIN EQUINE INFLUENZA VIRUS GROWN IN CLDK CELLS WITH AND WITHOUT TRYPSIN | | | |
|---|---|---|---|
| Amt. Trypsin | Titer (EID$_{50}$/ml) | | Fold Increase |
| (μg/ml) | Input | Harvest | With Trypsin |
| 10 | $10^{2.9}$ | $10^{9.2}$ | 1.000 |
| 10 | $10^{2.9}$ | $10^{8.5}$ | 200 |
| 10 | $10^{3.2}$ | $10^{8.2}$ | 100 |
| 10 | $10^{3.2}$ | $10^{10.0}$ | 6.310 |
| 10 | $10^{3.1}$ | $10^{14.5}$ | 199,526.232 |
| 15 | $10^{3.1}$ | $10^{8.9}$ | 501 |

Incorporation of trypsin into the growth medium produced a geometric mean increase of 3.2 logs or 1711 times as many virus particles/ml during production of the Miami strain.

EXAMPLE 2

A sample of virulent type A1 Equine Influenza virus was obtained from the University of Pennsylvania Medical School. The strain, designated Pennsylvania (A1), has been isolated from a horse and passaged in chick embryo six times. The strain has undergone further chick embryo passage and is being used for tissue culture production at passages 12–17.

The preferred method of tissue culture propagation of the A1 strain involves infection of a suspension of CLDK cells prior to monolayer formation. CLDK cells at a concentration of approximately $10^{5.5}$/ml, Pennsylvania strain of virus at an EID$_{50}$ titer of $10^{3.0}$/ml to $10^{5.0}$/ml, and Hank's Minimum Essential Medium (MEMH) supplemented with the ingredients listed below are incubated at 25° C. while being mixed on a magnetic stirrer in a closed, sterile Ehrlenmeyer flask. The pH is maintained at 6.7–6.8 with I N HCI during the 2–3 hour incubation period.

Supplemented MEMH
50% Dextrose, 2.6 ml/l
MEM Vitamins, 30 ml/l (Gibco)
Non-Essential Amino Acids, 10 ml/l (Gibco)
L-Glutamine, 10 ml/l (Gibco)
Neomycin Sulfate, 30,000 meg./l
Polymyxin B, 30,000 units/l
Mycostatin, 25,000 units/l After this suspension incubation, 10 ml aliquots of the cell virus suspension are added to roller bottles containing 1 liter of MEMH supplemented as listed above and containing 5% Fetal Calf Serum. The roller bottles are incubated at 34°–35° C. until the monolayer is confluent (approximately 48–72 hours) after which 20 ml of a sterile 1 mg/ml trypsin solution (Sigma 1:250) is added to each roller bottle. The roller bottles are again incubated at 34°–35° C. until the maximum cytopathic effect is observed (3–5 days). The virus fluids are harvested by vigorously shaking each roller bottle to remove cells which remain attached and transferring cells and fluids to a sterile container for further processing.

Harvest EID$_{50}$ titers of the A1 Influenza virus grown using this technique are shown in Table 2. Also, see FIG. 2. A comparison is made with A1 virus grown by the same method excluding trypsin

TABLE 2

| EID$_{50}$ TITERS OF PENNSYLVANIA STRAIN EQUINE INFLUENZA VIRUS GROWN IN CLDK CELLS WITH AND WITHOUT TRYPSIN | | | |
|---|---|---|---|
| Amt. Trypsin | Titer (EID$_{50}$/ml) | | Fold Increase |
| (μg/ml) | Input | Harvest | With Trypsin |
| None | $10^{5.3}$ | $10^{5.9}$ | — |
| None | $10^{4.9}$ | $10^{5.4}$ | — |
| 10 | $10^{5.3}$ | $10^{7.4}$ | 50 |
| 10 | $10^{4.9}$ | $10^{6.8}$ | 13 |
| 10 | $10^{5.1}$ | $10^{8.0}$ | 200 |
| 20 | $10^{5.3}$ | $10^{8.7}$ | 1.000 |
| 20 | $10^{4.9}$ | $10^{8.5}$ | 631 |
| 20 | $10^{5.0}$ | $10^{7.1}$ | 25 |
| 20 | $10^{4.9}$ | $10^{8.3}$ | 398 |
| 20 | $10^{3.2}$ | $10^{9.2}$ | 3.162 |
| 20 | $10^{3.2}$ | $10^{7.5}$ | 63 |
| 20 | $10^{3.2}$ | $10^{8.2}$ | 316 |

Incorporation of trypsin into the growth medium produced a geometric mean increase of 2.3 logs or 187 times as many virus particles/ml during production of the Pennsylvania strain.

EXAMPLE 3

A strain of Human Influenza virus designated B/Hong Kong/5/72 (BX-1) was received from The Center for Disease Control in Atlanta, Ga. This was passaged once in embryonated chicken eggs and frozen at −70° C. as working seed virus.

The preferred method of tissue culture propagation of the B/Hong Kong/5/72 strain involves infection of a young confluent monolayer of CLDK cells similar to that in Example 1. Cells are grown as described in Example 1. Growth medium is removed from cells and discarded. Cells are then infected with virus diluted in the inoculating medium listed in Example 1 to an EID$_{50}$ titer of approximately $10^{3.0-5.0}$/ml. The inoculum consists of a volume equivalent to 33.3% of the final harvest volume. Containers are incubated at at 34°–35° C. for 40–48 hours after which the remaining medium (66.7%) containing 12 μg/ml of trypsin solution (0.1 g/100 ml) is added to each container. Incubation at 34°–35° C. is continued until the maximum cytopathic effect is observed (48–72 hours) at which time the virus fluids are harvested. Harvest involves vigorously shaking each container to remove cells and transferring cells and fluids to a sterile container for further processing.

Harvest EID$_{50}$ titers of B/Hong Kong/5/72 Influenza virus grown using this technique are shown in Table 3. Also, see FIG. 3. A comparison is made with this strain grown by the same method but without adding trypsin.

TABLE 3

| EID$_{50}$ TITERS OF B/HONG KONG/5/72 STRAIN HUMAN INFLUENZA VIRUS GROWN IN CLDK CELLS WITH AND WITHOUT TRYPSIN | | | |
|---|---|---|---|
| Amt. Trypsin | Titer (EID$_{50}$/ml) | | Fold Increase |
| (μg/ml) | Input | Harvest | With Trypsin |
| None | $10^{3.2}$ | $10^{6.0}$ | — |
| None | $10^{5.7}$ | $10^{6.4}$ | — |
| 8 | $10^{3.0}$ | $10^{8.7}$ | 316 |
| 8 | $10^{2.0}$ | $10^{9.0}$ | 631 |
| 8 | $10^{4.5}$ | $10^{9.5}$ | 1.995 |
| 8 | $10^{3.5}$ | $>10^{10.2}$ | >10.000 |

Incorporation of trypsin into the growth medium produces a geometric mean increase of 3.1 logs or 1412 times as many virus particles during production of the B/Hong Kong strain.

EXAMPLE 4

A strain of Human Influenza virus designated A/Texas/1/77 was received from The Center for Disease Control in Atlanta, Ga. This was passaged once in embryonated chicken eggs and frozen at −70° C. as working seed virus.

The preferred method of tissue culture propagation of the A/Texas/1/77 strain is that described in total in Example 3.

Harvest $EID_{50}$ titers of A/Texas/1/77 Human Influenza virus grown using this technique are shown in Table 4. Also, see FIG. 4. A comparison is made with this strain grown by the same method but without adding trypsin.

TABLE 4

$EID_{50}$ TITERS OF A/TEXAS/1/77 STRAIN HUMAN INFLUENZA VIRUS GROWN IN CLDK CELLS WITH AND WITHOUT TRYPSIN

| Amt. Trypsin (μg/ml) | Titer ($EID_{50}$/ml) Input | Harvest | Fold Increase With Trypsin |
|---|---|---|---|
| None | — | $10^{5.2}$ | — |
| 8 | $10^{5.1}$ | $10^{8.9}$ | 5.012 |
| 8 | $10^{4.1}$ | $>10^{10.2}$ | >100.000 |
| 10 | $10^{3.0}$ | $10^{8.3}$ | 1.259 |
| 10 | $10^{2.0}$ | $10^{9.8}$ | 39.811 |

Incorporation of trypsin with the growth medium produced a geometric mean increase of 4.1 logs or 12590 times as many virus particles/ml during production of the A/Texas strain.

EXAMPLE 5

A strain of Human Influenza virus designated A/USSR/90/77 was received from the Center for Disease Control in Atlanta, Ga. This was passaged once in embryonated chicken eggs and frozen at −70° C. as working seed virus.

The preferred method of tissue culture propagation of the A/USSR/90/77 strain is that described in total in Example 3.

Harvest $EID_{50}$ titers of A/USSR/90/77 Human Influenza virus grown using this technique are shown in Table 5. Also, see FIG. 5. A comparison is made with this strain grown by the sane method but without adding trypsin.

TABLE 5

$EID_{50}$ TITERS OF A/USSR/90/77 STRAIN HUMAN INFLUENZA VIRUS GROWN IN CLDK CELLS WITH AND WITHOUT TRYPSIN

| Amt. Trypsin (μg/ml) | Titer ($EID_{50}$/ml) Input | Harvest | Fold Increase With Trypsin |
|---|---|---|---|
| None | $10^{4.0}$ | $10^{6.3}$ | — |
| 10 | $10^{4.0}$ | $10^{8.7}$ | 251 |
| 10 | $10^{4.0}$ | $10^{9.0}$ | 501 |
| 10 | $10^{4.5}$ | $10^{8.4}$ | 126 |

Incorporation of trypsin into the growth medium produced a geometric mean increase of 2.4 logs or 251 times as many virus particles/ml during production of the A/USSR strain. VACCINE PREPARATION

EXAMPLE 6-VIRUS ATTENUATION

Attenuation of the virus from harvested fluids of Example 1 is accomplished chemically or by standard serial passages including terminal dilution passage techniques wherein a sufficient number of passages in a susceptible cell culture is employed until the virus is rendered non-pathogenic without loss of immunogenicity. A vaccine prepared in these manners will stimulate an immune response in animals susceptible to disease without producing the clinical sysmptoms normally due to the virulent agent to any significant degree. The propagation can be done in the same or different tissues as those employed in the preceding passage.

EXAMPLE 7-VIRUS INACTIVATION

The technique is similar to that described in Examples 1 and 2 but the harvest viral ledan fluids are further processed by inactivation with 0.1% concentration of formaldehyde (range 0.05 to 0.2%) and the treated material is incubated at 4° C. for 10 to 14 days. Testing of the final inactivated viral preparation showed it to be free from live virus. Adjuvants known to the art, such as aluminum hydroxide, alum, aluminum phosphate, Freund's, or those described in U.S. Pat. Nos. 3,790,665 and 3,919,411 may be added. The preferred adjuvant of this disclosure and that used in our vaccine is an acrylic acid polymer crosslinked with a polyallylsaccharide (Carbopol 934 P) similar to that described in the above patents.

EXAMPLE 8-INACTIVATED VIRUS VACCINE PREPARATION AND USE

A 1.0 ml equine dose consists of 0.45 ml of the Pennsylvania (A1) strain, 0.45 ml of the Miami (A2) strain and 0.10 ml of the Carbopol adjuvant. Equal parts of the inactivated vaccine strains obtained from Example 7 were mixed and 1 ml aliquots administered to 19 horses by the intramuscular route. No clinical disease or symptoms of influenza were noted in any of the horses after vaccination. Antibody titers against both Equine Influenza A1 and Equine Influenza A2 were obtained on blood sera of all animals at 2, 4, and 8 weeks following inoculation. These are compared to the pre-inoculation levels (Table 6) using the standard haemagglutination inhibition test (DIAGNOSTIC PROCEDURES for Viral and Rickettsial Infections, Fourth Edition; Lenette and Schmidt, pp. 665–66 (1969). American Public Health Association, New York, N.Y. 10019).

TABLE 6

ANTIBODY RESPONSES (HAEMAGGLUTINATION INHIBITION)

| Horse No. | Equine Influenza A1 Pre. | 2 wk. | 4 wk.* | 8 wk. | Equine Influenza A2 Pre. | 2 wk. | 4 wk.* | 8 wk. |
|---|---|---|---|---|---|---|---|---|
| 2 | <8 | 8.192 | 8.192 | 8.192 | <8 | 512 | 128 | 256 |
| 11 | <8 | 128 | 256 | 128 | <8 | 64 | 1.024 | 64 |
| 13 | <8 | 128 | 256 | 2.048 | <8 | 256 | 256 | 1.024 |
| 19 | <8 | 256 | 64 | 64 | <8 | 128 | 128 | 64 |
| 21 | <8 | 128 | 64 | 512 | <8 | 64 | 64 | 512 |
| 23 | <8 | 256 | 128 | 128 | <8 | 512 | 512 | 128 |
| 29 | <8 | 128 | 32 | 1.024 | <8 | 256 | 64 | 128 |
| 32 | <8 | 1.024 | 256 | 2.048 | <8 | 64 | 64 | 128 |
| 37 | <8 | 128 | 32 | 512 | <8 | 64 | 32 | 64 |
| 38 | <8 | 1.024 | 512 | 1.024 | <8 | 512 | 256 | 64 |
| 40 | <8 | 256 | 128 | 1.024 | <8 | 128 | 128 | 128 |
| 55 | <8 | 512 | 512 | 8.192 | <8 | 512 | 256 | 256 |
| 61 | <8 | 512 | 64 | 256 | <8 | 1.024 | 128 | 128 |
| 68 | <8 | 128 | 32 | 128 | <8 | 512 | 256 | 256 |
| 79 | <8 | 64 | 128 | 2.048 | <8 | 256 | 128 | 128 |
| 121 | <8 | <8 | 32 | 512 | <8 | 1.024 | 256 | 64 |
| 125 | <8 | 256 | 32 | 128 | <8 | 256 | 128 | 128 |
| 128 | <8 | 512 | 128 | 512 | <8 | 256 | 128 | 256 |

TABLE 6-continued

| ANTIBODY RESPONSES (HAEMAGGLUTINATION INHIBITION) | | | | | | | | |
|---|---|---|---|---|---|---|---|---|
| | Equine Influenza A1 | | | | Equine Influenza A2 | | | |
| Horse No. | Pre. | 2 wk. | 4 wk.* | 8 wk. | Pre. | 2 wk. | 4 wk.* | 8 wk. |
| 129 | <8 | 256 | 128 | 2.048 | <8 | 512 | 512 | 256 |

*Day of booster

As can be seen from Table 6, antibody developed to both viral antigens in horses receiving the inoculations. These vaccinates would be immune to Equine Influenza since antibody titers in excess of 1:20 to A2 and 1:60 for A1 are accepted as being protective by the National Veterinary Services Laboratories of the U.S. Department of Agriculture.

Clinical trials in 420 horses of various breeds and ages showed the vaccine to be safe and to produce no untoward reactions after intramuscular inoculation.

EXAMPLE 9-ATTENUATED VIRUS VACCINE USE

Three horses were given 5 ml of the live, attenuated Equine Influenza A2 vaccine strain of Example 6 by the intranasal route. No clinical disease or symptoms of influenza were noted in any of the horses after vaccination. Antibody titers against the vaccine strain were obtained on blood sera of all animals at 1, 2, and 4 weeks following inoculation and compared to the pre-inoculation level using the standard haemagglutination inhibition test (HAI).

TABLE 7

| ANTIBODY RESPONSE (HAI) EQUINE INFLUENZA A2 | | | | |
|---|---|---|---|---|
| Horse No. | Pre | 1 week | 2 weeks | 4 weeks |
| 19 | <8 | 128 | 256 | 128 |
| 23 | 8 | 64 | 128 | 128 |
| 61 | <8 | 128 | 256 | 128 |

Once again, the antibody titers obtained are greater than required for protection.

It should be noted that this disclosure is concerned with both a novel influenza culture system and the use of the medium to produce a novel influenza vaccine. The liquid cell culture system used in this invention entains the use of susceptible cells, influenza viruses, a nutrient medium and a proteolytic enzyme, but unlike past systems (e.g. the Tobita et al. reference), does not require the use of agar which reduces the system to a semi-solid state. The exclusion of the agar thus enables large scale production of viruses in the conventional manner known to the art and results in the production of viral fluids of sufficiently high titers for the preparation of vaccines.

The influenza vaccine preparation itself comprises effective amounts of one or more strains of given influenza virus particles and a pharmaceutically acceptable carrier, the total preparation, preferably in aqueous form, being substantially free of reactive proteins such as egg proteins. As used herein, the term substantially free of egg protein means that the only possible source of egg protein in the vaccine preparations is the seed virus which is diluted >1:100,000.

The vaccines are administered to animals by various routes, including intramuscular, intravenous, subcutaneous, intratracheal, intranasal, or by aerosol spray and the vaccines are contemplated for beneficial use in a variety of animals, including human, equine, porcine, and avian groups.

The viral preparations produced by this invention may be diluted with water to adjust their potency, and they may have added to them stabilizers such as sucrose, dextrose, lactose, or other non-toxic substances. The viral preparations may be desiccated by freeze drying for storage purposes or for subsequent formulation into attenuated vaccines or they may be chemically inactivated for the preparation of killed virus vaccines.

It can be appreciated that all of the virus strains of the above Examples fall into the Genus Influenza virus within the Orthomyxoviridae Classification. See, for example, Principles of Animal Virology, W. K. Joklik, Appleton-Century-Crofts/ 1980, pages 52 and 53. Accordingly, it is intended that this disclosure should enable one skilled in the art to use the above-described methods to prepare high-titered (e.g. $EID_{50}$/ml of at least about $10^7$) vaccines for any virus of the Orthomyxoviridae class. Regarding the tissue culture cell use, it is only necessary that the cell be susceptible to the specific virus strain of the Genus Influenza from which a vaccine is to be prepared. It is thought to be well within the skill of a component microbiologist or virologist to select such a susceptible cell vis-a-vis a given virus strain of the Orthomyxoviridae class. In a typical situation a virologist would select the best growing cells from known cell stocks, infect them with the virus strain in the presence of protease, and observe for production of cytopathic effect. Fluids from all infected cells producing cytopathic effects would be titrated for virus concentration. Experiments in our laboratory indicated that many cell types including Bovine Kidney. Vero, and Canine Kidney support growth of Influenza virus when using the procedure described herein.

As described above, an essential feature of the present invention is that the incubation (virus replication) step be in the presence of a protease under conditions sufficient to overcome the one-step growth cycle of the virus. As can be seen from the data, and especially as shown by the Figures, when a protease (such as trypsin) is included (in the range of about 4–25 micrograms/ml culture medium) in the culture, an $EID_{50}$/ml titer of at least about $10^7$ is obtained. Obtaining such a high titer (in many cases $\geqq 10^9$ $EID_{50}$/ml) now provides a means for economically making Influenza Virus vaccines without the use of costly embryonated eggs. It should be pointed out that the surprisingly high titer results shown in the Tables and Figures are due solely to the presence of the indicated amounts of the protease (trypsin) in the infected tissue culture. In cases where trypsinization techniques are used (e.g. in removing cell layers from a surface, using significantly larger amounts of the enzyme, 0.5 to 1.0 mg/ml) it is common practice, prior to virus infection, to remove or inactivate the enzyme to avoid digestion of the cells. Removal of the trypsin is accomplished by simply centrifuging the trypsin/cell mixture and pouring off the supernatant trypsin solution or by simply diluting the active trypsin out of the system. Alternatively, any remaining active trypsin may be neutralized (inactivated) by assuring the presence of known trypsin activity neutralizers (i.e. the presence of serum, used for nutrative purposes in the cell culture, will assure the inactivation of trypsin and preclude the carry over of active trypsin to the virus-infected cell culture). In either case (trypsin removal or inactivation), it is important to note that the pre-infection liquid cell culture of this disclosure is substantially free of proteolytic activity. As used herein, the expression substantially free of proteolytic activity means that whatever activity may remain it is not sufficient to overcome single step growth cycle. Additional fresh trypsin may be added to accomplish the virus replication required by the invention disclosed herein. Even if there were some residual trypsin which somehow escaped removal or inactivation techniques such residual amounts would correspond to the "zero" amounts in the Figures (the controls) since those cells had been transferred using conventional trypsinizing technique and, hence, not be present in quantities sufficient to lead to the high titer results. Because of the use of the protease during the replication step (in contrast to any prior trypsination steps which would eliminate any such protease activity), the final vaccine product of this invention will contain measurable amounts of protease activity. In the case of trypsin use, the final Influenza virus vaccine will typically contain at least 1 to 10 units of trypsin activity per milliliter of Vaccine preparation (e.g. vaccine in an aqueous carried), a feature not associated with known Influenza virus vaccines. One unit is defined as the $\Delta A_{253}$ of 0.001/min. with N alpha-benyl-L-arginine ethylester (BAEE). This feature helps distinguish the vaccine of this invention from those of the prior art. Thus, the typical vaccine of this invention contains virus grown to at least $10^7$ $EID_{50}$/ml, a trypsin activity of at least about 1 to 10 units per mil, and includes a pharmaceutically acceptable liquid carrier which is relatively clear, non-cloudy, and essentially free of egg protein. As used herein, the expression pharmaceutically acceptable liquid carrier includes a tissue culture fluid which consists of a basal salts solution, amino acids, vitamins, other growth nutrients, antibiotics and a fungistat.

It should be understood that the above examples are merely illustrative and that the scope of this disclosure should be limited only by the following claims.

We claim:

1. A method of preparing an influenza virus vaccine which comprises the steps of:

(a) infecting a portion of the cells of a liquid cell culture substantially free of proteolytic enzyme with an influenza virus;

(b) incubating the infected culture in the presence of a proteolytic enzyme under conditions sufficient to assure further infection and replication of the virus in cells other than the originally infected cells and an $EID_{50}$/ml titer of at least about $10^7$;

(c) harvesting the virus from the culture, and;

(d) preparing a vaccine from the harvested virus.

2. The method of claim 1 wherein the cell culture of step (a) comprises a confluent monolayer of cells.

3. The method of claim 1 wherein the cell culture of step (a) comprises a liquid suspension of cells.

4. The method of claim 1 wherein the vaccine preparation of step (d) includes the step of inactivating the harvested virus.

5. The method of claim 1 wherein the vaccine preparation of step (d) includes the step of attenuating the harvested virus.

6. The method of claim 1 wherein the proteolytic enzyme of step (b) is selected from trypsin, chymotrypsin, pepsin, pancreatin, papain, pronase and carboxypeptidase.

7. The method of claim 1 wherein the virus is an equine influenza virus.

8. The method of claim 7 wherein the virus is a strain selected from equine influenza A1 and equine influenza A2 virus strains.

9. The method of claim 1 wherein the virus is a human influenza virus.

10. The method of claim 9 wherein the virus is selected from B/Hong Kong, A/Texas, and A/USSR virus strains.

11. The method of claim 1 wherein the cells of the cell culture are dog kidney cells.

12. The method of claim 1 wherein the cell culture of step (a) is a dog kidney cell culture, the virus of step (a) is an equine influenza virus, and the enzyme of step (b) is trypsin.

13. The method of claim 1 wherein the cell culture of step (a) is a dog kidney cell culture, the virus of step (a) is a human influenza virus, and the enzyme of step (b) is trypsin.

14. The method of claim 1 wherein the enzyme of step (b) is present in an amount sufficient to assure infectivity and replication of the virus in culture cells other than the cells comprising that portion infected in step (a).

15. The method of claim 14 wherein the amount of trypsin ranges from about 4 to about 25 micrograms per ml of culture media.

*16. A method of preparing an influenza virus vaccine which comprises the steps of*

*(a) infecting a portion of the cells of a liquid cell culture substantially free of proteolytic enzyme with an influenza virus;*

*(b) incubating the already infected culture in the presence of a proteolytic enzyme present in an amount sufficient to assure further infection and replication of the virus in cells other than the originally infected cells until the $EID_{50}$/ml titer has increased by a factor of at least about $10^2$;*

*(c) harvesting the virus from the culture; and*

*(d) preparing a vaccine from the harvested virus.*

*17. The method of claim 16 wherein the proteolytic enzyme is present at a concentration of between about 4 and 25 micrograms per ml of culture medium.*

*18. The method of claim 16 wherein the cells are incubated with the infecting inoculum for at least about one hour before the proteolytic enzyme is added.*

*19. The method of claim 16 wherein the proteolytic enzyme is selected from the group consisting of trypsin, chymotrypsin, pepsin, pancreatin, pronase and carboxypeptidase.*

*20. The method of claim 19 wherein the proteolytic enzyme is trypsin.*

*21. The method of claim 20 wherein the trypsin is present at a concentration of between about 4 and 25 micrograms per ml of culture medium.*

*22. The method of claim 21 wherein the cells are incubated with the infecting inoculum for at least about one hour before the trypsin is added.*

*23. The method of claim 22 wherein the virus is an equine influenza virus.*

*24. The method of claim 23 wherein the virus is a strain selected from the group consisting of the A1 and A2 equine influenza strains.*

*25. The method of claim 22 wherein the virus is a human influenza virus.*

*26. The method of claim 25 wherein the virus is selected from the group consisting of the B/Hong Kong, A/Texas, and A/USSR human influenza strains.*

*27. The method of claim 23 or claim 24 or claim 25 or claim 26 wherein the cells of the cell culture are dog kidney cells.*

*28. The method of claim 16 wherein the cell culture which is infected is a liquid cell suspension culture.*

*29. The method of claim 28 wherein the cell culture is maintained as a liquid cell suspension culture until the virus is harvested.*

*30. The method of claim 16 wherein the cell culture is incubated with the proteolytic enzyme as a confluent monolayer of cells.*

*31. The method of claim 30 wherein the cell culture is incubated with the proteolytic enzyme in a roller bottle, Roux bottle or Povitsky flask.*

*32. The method of claim 31 wherein the cell culture is incubated with the proteolytic enzyme in a roller bottle.*

*33. A method of preparing an equine influenza vaccine which is essentially free of egg proteins which comprises the steps of*

*(a) incubating a liquid cell culture with an amount of an inoculum of the influenza virus sufficient to infect a portion but not all of the cells in the absence of any substantial amount of proteolytic enzyme for between about 1 to 72 hours;*

*(b) combining the infected cell culture with between about 4 and 25 micrograms per ml of culture of trypsin and incubating until maximum cytopathic effect is observed and the $EID_{50}$/ml titer has increased by a factor of at least about $10^2$;*

*(c) harvesting the virus from the culture; and*

*(d) preparing a vaccine from the culture.*

*34. The method of claim 33 wherein the cells of the culture are dog kidney cells.*

* * * * *

UNITED STATES PATENT AND TRADEMARK OFFICE

CERTIFICATE OF CORRECTION

PATENT NO. : RE. 33,164

DATED : February 13, 1990

INVENTOR(S) : Karen K. Brown et al

It is certified that error appears in the above-identified patent and that said Letters Patent is hereby corrected as shown below:

On the face of the patent at [64] Patent No. "5,005,139" should be corrected to --4,500,513--.

At column 4, line 11, "rhinotrachetis" should be --rhinotracheitis--.

At columns 6, 7, 8, 9, 10 and 11 in the Tables identifed as Table 1, Table 1-continued, Table 2, Table 3, Table 4, Table 6 and Table 6-continued, corrections are required as follows:

In Table 1, Table 1-continued, Tables 2, 3 and 4 at the fourth column of the table under the heading "Fold Increase with Trypsin", the period should be deleted and a comma inserted as follows: "1.000" to --1,000--. in all instances, "6.310" to --6,310--, "3.162" to --3,162--, "1.995" to --1,995--, "10.000" to --10,000--, "5.012" to --5,012--, "100.000" to --100,000--, "1.259" to --1,259--, "39.811" to --39,811--.

In Table 6 and Table 6-continued, please delete the table and substitute the corrected table as set forth on page -2-. The new table has been corrected in all instances of four digit numbers where a period is printed instead of a comma.

UNITED STATES PATENT AND TRADEMARK OFFICE

CERTIFICATE OF CORRECTION

PATENT NO. : RE. 33,164

DATED : February 13, 1990

INVENTOR(S) : Karen K. Brown et al

It is certified that error appears in the above-identified patent and that said Letters Patent is hereby corrected as shown below:

TABLE 6

ANTIBODY RESPONSES (HAEMAGGLUTINATION INHIBITION)

| Horse | Equine Influenza A1 | | | | Equine Influenza A2 | | | |
|---|---|---|---|---|---|---|---|---|
| No. | Pre. | 2 wk. | 4 wk.* | 8 wk. | Pre. | 2 wk. | 4 wk.* | 8 wk. |
| 2 | <8 | 8,192 | 8,192 | 8,192 | <8 | 512 | 128 | 256 |
| 11 | <8 | 128 | 256 | 128 | <8 | 64 | 1,024 | 64 |
| 13 | <8 | 128 | 256 | 2,048 | <8 | 256 | 256 | 1,024 |
| 19 | <8 | 256 | 64 | 64 | <8 | 128 | 128 | 64 |
| 21 | <8 | 128 | 64 | 512 | <8 | 64 | 64 | 512 |
| 23 | <8 | 256 | 128 | 128 | <8 | 512 | 512 | 128 |
| 29 | <8 | 128 | 32 | 1,024 | <8 | 256 | 64 | 128 |
| 32 | <8 | 1,024 | 256 | 2,048 | <8 | 64 | 64 | 128 |
| 37 | <8 | 128 | 32 | 512 | <8 | 64 | 32 | 64 |
| 38 | <8 | 1,024 | 512 | 1,024 | <8 | 512 | 256 | 64 |
| 40 | <8 | 256 | 128 | 1,024 | <8 | 128 | 128 | 128 |
| 55 | <8 | 512 | 512 | 8,192 | <8 | 512 | 256 | 256 |
| 61 | <8 | 512 | 64 | 256 | <8 | 1,024 | 128 | 128 |
| 68 | <8 | 128 | 32 | 128 | <8 | 512 | 256 | 256 |
| 79 | <8 | 64 | 128 | 2,048 | <8 | 256 | 128 | 128 |
| 121 | <8 | <8 | 32 | 512 | <8 | 1,024 | 256 | 64 |
| 125 | <8 | 256 | 32 | 128 | <8 | 256 | 128 | 128 |
| 128 | <8 | 512 | 128 | 512 | <8 | 256 | 128 | 256 |
| 129 | <8 | 256 | 128 | 2,048 | <8 | 512 | 512 | 256 |

*Day of Booster

UNITED STATES PATENT AND TRADEMARK OFFICE

CERTIFICATE OF CORRECTION

PATENT NO. : Re. 33, 164

DATED : February 13, 1990

INVENTOR(S) : Karen K. Brown et al

It is certified that error appears in the above-identified patent and that said Letters Patent is hereby corrected as shown below:

At column 9, line 63, "VACCINE PREPARATION" should be moved to a new line.

At column 13, line 16, "trypsination" should be --trypsinization--.

Signed and Sealed this

Third Day of December, 1991

*Attest:*

HARRY F. MANBECK, JR.

*Attesting Officer*

*Commissioner of Patents and Trademarks*